(12) United States Patent
Liao et al.

(10) Patent No.: US 7,190,273 B2
(45) Date of Patent: Mar. 13, 2007

(54) JOINT ENDOPROSTHESIS WITH AMBIENT CONDITION SENSING

(75) Inventors: Yen-Shuo Liao, Warsaw, IN (US); Mark DiSilvestro, Fort Wayne, IN (US)

(73) Assignee: DePuy Products, Inc., Warsaw, IN (US)

(*) Notice: Subject to any disclaimer, the term of this patent is extended or adjusted under 35 U.S.C. 154(b) by 103 days.

(21) Appl. No.: 10/813,803

(22) Filed: Mar. 31, 2004

(65) Prior Publication Data
US 2005/0012610 A1    Jan. 20, 2005

Related U.S. Application Data

(60) Provisional application No. 60/486,615, filed on Jul. 11, 2003, provisional application No. 60/486,762, filed on Jul. 11, 2003.

(51) Int. Cl.
*G08B 23/00* (2006.01)
(52) U.S. Cl. .............................. 340/573.1; 340/539.24; 340/581; 600/30; 600/340; 600/549; 128/903
(58) Field of Classification Search ............ 340/573.1, 340/581, 539.1, 539.12, 539.24; 600/300, 600/309, 340, 474, 549, 30; 128/899, 903
See application file for complete search history.

(56) References Cited

U.S. PATENT DOCUMENTS

| | | | |
|---|---|---|---|
| 5,113,869 A * | 5/1992 | Nappholz et al. ........... | 600/508 |
| 5,300,120 A | 4/1994 | Knapp et al. | |
| 5,518,008 A * | 5/1996 | Cucchiaro et al. .......... | 600/590 |
| 6,155,267 A * | 12/2000 | Nelson ........................ | 128/899 |
| 6,272,379 B1 * | 8/2001 | Fischell et al. ................ | 607/5 |
| 6,402,689 B1 * | 6/2002 | Scarantino et al. ......... | 600/300 |
| 6,442,413 B1 * | 8/2002 | Silver .......................... | 600/345 |
| 6,447,448 B1 * | 9/2002 | Ishikawa et al. ............ | 600/300 |
| 6,689,056 B1 | 2/2004 | Kilcoyne et al. | |
| 6,890,303 B2 * | 5/2005 | Fitz .............................. | 600/486 |
| 6,917,831 B2 * | 7/2005 | Bloemer et al. .............. | 607/16 |

* cited by examiner

*Primary Examiner*—Davetta W. Goins
(74) *Attorney, Agent, or Firm*—Maginot, Moore & Beck

(57) ABSTRACT

A system for monitoring the ambient conditions of a mammalian joint, and particularly a joint that has been instrumented with a joint endoprosthesis includes a sensor supported by a component of the joint endoprosthesis. The system includes a transmission element that is also supported within the body of the patient, preferably within the endoprosthesis. The transmission element transmits a signal indicative of the sensed ambient condition within the instrumented joint. For example, the sensor can be a temperature sensor used to evaluate the temperature within a joint, such as a hip joint, during activity or exercise by the patient.

19 Claims, 3 Drawing Sheets

JOINT ENDOPROSTHESIS WITH AMBIENT CONDITION SENSING

CROSS-REFERENCE TO RELATED APPLICATIONS

This application claims priority to U.S. Provisional Patent Application No. 60/486,615, entitled "In Vivo Joint Space Measurement Device and Method", filed on Jul. 11, 2003, and naming one of the co-inventors of the present application. This application also claims priority to U.S. Provisional Patent Application No. 60/486,762, entitled "In Vivo Joint Implant Cycle Counter", filed on Jul. 11, 2003, and naming one of the co-inventors of the present application.

FIELD OF THE INVENTION

The present invention relates to orthopaedic components configured for implantation within a patient. In particular, the invention concerns systems and methods for evaluating the ambient conditions within a joint space.

BACKGROUND OF THE INVENTION

Replacement of human joints, such as the knee, shoulder, elbow and hip, has become a more and more frequent medical treatment. Longer life spans mean that the joints endure more wear and tear. More sports activities mean greater likelihood of serious joint injuries. Treatment of injuries, wear and disease in human joints has progressed from the use of orthotics to mask the problem, to fusion of the joint, to the use of prostheses to replace the damaged joint component(s).

Joint endoprostheses have been developed to replace virtually every human joint. The efficacy and success of these orthopaedic components or implants has steadily increased over the years as improvements in materials, manufacturing and design are developed. New machining processes and material coatings have been developed that enhance the fixation of the implant within the natural bone of a patient. Alloys and ceramics have been developed that emulate the strength of natural bone, while still preserving the biomechanical attributes of the joint being repaired. Bearing surfaces have been improved to increase the bearing life.

In spite of these improvements in endoprosthesis design and in the surgical procedures to implant these joint components, it is still difficult to control or emulate the ambient conditions of an intact mammalian joint. For instance, any articulating endoprosthesis necessarily generates heat from friction between the moving components. Excessive temperatures can lead to boney and soft tissue damage and even necrosis in a joint. Materials choice and smooth machining techniques can greatly reduce the friction between articulating parts, but in spite of these efforts joint over-heating may be a problem.

In an ideally constructed endoprosthesis, friction may only become a problem as the bearing surfaces wear. Since the prosthetic bearing components are not regenerative, the surfaces of these components will inevitably wear, especially in an active patient. As the bearing surfaces wear and roughen, friction increases, which may result in a noticeable, and even dangerous, increase in joint temperature. An awareness of this ambient condition of the joint can be used to assist in diagnosis of early problems and to determine when a revision of the endoprosthesis will be necessary before the bone and surrounding soft tissue is damaged.

SUMMARY OF THE INVENTION

In order to address these problems, the present invention contemplates a system for monitoring the ambient conditions of a mammalian joint, and particularly a joint that has been instrumented with a joint endoprosthesis. In one embodiment of the invention, the ambient condition is the temperature within the joint. In this embodiment, a temperature sensor is supported by a component of a joint endoprosthesis, such as an articulating component of the endoprosthesis. The temperature sensor communicates a signal indicative of the ambient temperature within the joint to a transmission element that is supported within the body of the patient. In a preferred embodiment, the transmission element is also supported within a component of the joint endoprosthesis.

The transmission element includes electrical or electronic elements operable to transmit a signal in relation to the temperature signal received from the temperature sensor. In one embodiment, the transmission element includes an antenna that transmits a signal outside the joint to a receiver. The receiver can include electrical or electronic elements that can translate the signal received from the transmission element into a human sensible format. For instance, the receiver can provide a visual display of the ambient temperature within the joint. Alternatively, or in addition, the receiver can issue an audible alarm if the sensed temperature exceeds a pre-determined threshold. A memory component can be associated with the receiver to maintain a retrievable history of the temperature within the joint.

In certain embodiments, the temperature sensor and transmitter are disposed within corresponding cavities defined in the orthopaedic component. The cavity is potted with a biologically compatible material, such as a bone cement. Preferably, the depth of the cavity for the temperature sensor is adequate for a meaningful temperature reading within the joint. Moreover, the temperature sensor is most preferably situated as close to an articulating surface of the joint as possible, since friction generated by movement of this surface is a primary cause of deleterious temperature increases within the joint. For instance, where the joint endoprosthesis is a hip prosthesis, the temperature sensor can be disposed in the acetabular cup or in the femoral head, since these components include the articulating surface for the hip prosthesis.

The transmission element can be configured to simply transmit the temperature signal generated by the sensor, or it can be configured to analyze the temperature signal. In the former case, the analysis of the temperature signal can occur in the receiver. The temperature signal can be evaluated to determine whether a critical temperature condition exists. For instance, it is known that sustained temperatures above 44° C. can cause necrosis of bone and soft tissues. The temperature signal can be first evaluated to determine whether the ambient temperature in the joint has reached this threshold temperature. It is contemplated that some conditioning of the temperature signal may be required. If the sensor is not in direct contact with the bone or surrounding soft tissue, any temperature value is necessarily less than the ambient condition due to the thermal conductivity of the medium supporting the temperature sensor. The temperature signal can be conditioned to account for this temperature differential to produce an accurate estimate of the ambient temperature in the joint.

The analysis of the temperature signal can also include a time element—i.e., to determine how long has the sensed temperature exceeded the temperature threshold. This time aspect of the analysis can be based on a time threshold, such as one minute of sustained temperature above the threshold. Alternatively, the analysis can be based on a time-temperature function in which the temperature threshold varies as a function of the length of time at that temperature. For example, ambient temperatures above 50° C. may be indicative of a serious problem so the time limit at this temperature may be relatively short, say 30 seconds. On the other hand, an ambient temperature below the necrosis threshold temperature may be sustainable for several minutes before a problem is indicated. This time-temperature function can be applied through appropriate circuitry or through on-board software that applies an equation or utilizes a table look-up.

In accordance with certain features of the invention, the system component resident with the joint endoprosthesis includes a power source to drive the temperature sensor and the transmission element. The power source can be self-contained, such as a battery, which is disposed within a component of the endoprosthesis. The power source can be passive, such as a power coil that derives its power from electromagnetic coupling with an external coil. This passive power source approach can utilize technology commonly used for RFID tags. As with the RFID technology, the passive power source can also constitute an antenna for transmitting the temperature signal outside the joint. With the passive power source approach, an external power source driving the external coil may be carried by the patient in proximity to the endoprosthesis, or may be placed in proximity to the endoprosthesis by a caregiver at the point of care.

The present invention contemplates sensing other ambient conditions of an instrumented mammalian joint. For instance, the pH of the soft tissue or fluids within the joint can provide an indication of the health of the joint following implantation of an endoprosthesis. The pH can provide an indication of the presence of an infection in the joint before the infection is manifested by outwardly sensible symptoms, such as inflammation of the surrounding skin. Thus, the temperature sensor can be replaced by a pH sensor, where the pH sensor is positioned so that it is in contact with the tissue within the joint. A similar sensor can be used to detect the presence of specific genes, proteins, bacteria, chemicals or fluids within the joint. Sensors of this type can often be passive, meaning that a chemical reaction in the sensor generates an electrical current that can be sensed by a transmission element.

It is one object of the present invention to provide a system that can sense ambient conditions within a mammalian joint. One benefit of this system is that it can detect potentially harmful conditions within the joint that could not otherwise be sensed. A further benefit of the invention is that it provides a mechanism for warning a patient or a surgeon of this potentially harmful condition in sufficient time to allow remedial or corrective action to be taken.

These and other objects and benefits of the invention will become apparent upon consideration of the following written description, taken together with the accompanying figures.

DESCRIPTION OF THE PREFERRED EMBODIMENTS

Figure 1:
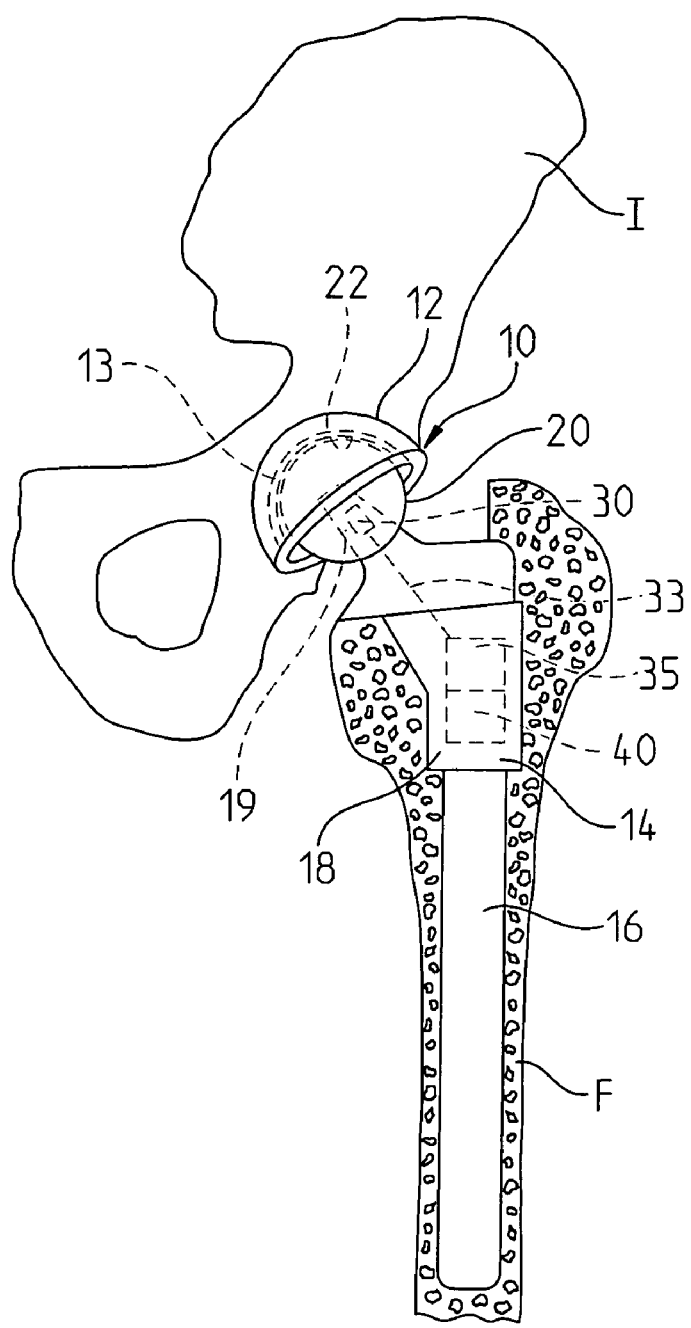
FIG. 1 is a cross-sectional view of a hip implant incorporating ambient condition sensing features of the present invention.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

The present invention contemplates a system for monitoring the ambient conditions within a mammalian joint. The invention is particularly suited for use with a human joint that has been replaced by an endoprosthesis. This invention is useful in joints that endure high loads over many cycles, such as the hip or knee, since these joints are especially susceptible to temperature increases due to unresolved friction in the endoprosthesis.

In accordance with one embodiment of the invention, a hip endoprosthesis 10 is depicted in FIG. 1. The endoprosthesis includes an acetabular cup 12 fixed within the ilium I. The cup includes a liner 13 that provides a low-friction articulating surface. The endoprosthesis further includes a femoral component 14 that is fixed within the prepared proximal end of the femur F. In particular, the femoral component includes a stem 16 implanted within the intramedullary canal of the femur F. The stem terminates in a proximal body 18 from which extends a neck 19. The neck carries a femoral head 20 mounted thereon, being configured to articulate within the liner 13 of the acetabular cup to define an articulating contact surface 22.

As with any surface of contact between moving components, the joint contact 22 between the two primary components of the hip endoprosthesis 10 generate a certain amount of friction. This friction results in a temperature increase in the articulating components, especially the acetabular cup 12 and the femoral head 20. This temperature increase is dissipated into the surrounding bone and soft tissue, resulting in an increase in ambient temperature within the joint. Research has demonstrated that necrosis starts when mammalian tissue is maintained at 44–47° C. for at least one minute [See, Eriksson et al. Scand J Plast. Reconstru. Surg. 1984; 18(3): 261–8].

In certain patient tests [see Bergman et al. Journal of Biomechanics 2001; 34: 421–428], a patient having a hip implant was instrumented with temperature sensors at various locations in the femoral head and stem . After over an hour of walking on a treadmill, the temperature at the center of the head reached about 43° C. In a laboratory hip simulation [see, Lu et al. Proc. Instn. Mech. Engrs. 1997;

[H], 211: 101–108], the temperature exceeded 50° C. after about three hours of continuous simulated walking. Finite element analysis has demonstrated that for a 50° C. temperature measured at the femoral head 0.5 mm to the articulating surface, the surface temperature could reach 100° C. Obviously, this temperature is well above the temperature at which tissue necrosis starts. Sustained ambient temperatures in this 100° C. range can cause severe damage to the bones and surrounding tissue. Consequently, the studies suggested that patients with hip implants to avoid any strenuous activity that might result in dangerous temperature increases in the hip joint.

Not all activity levels lead to unhealthy temperatures in the instrumented joint. Rather than avoid physical activity altogether, it is preferable that a patient be permitted to engage in healthy exercise, such as walking. The present invention provides a system for monitoring the ambient temperature of the joint and issuing a warning when the temperature reaches a pre-determined threshold value. The patient can then stop or reduce the activity level until the temperature returns to an acceptable value.

Thus, in accordance with one aspect of the invention, a sensor 30 is supported by one of the components of the endoprosthesis 10. In the illustrated embodiment, the sensor is supported in the neck 19 of the proximal body 18. Alternatively, the sensor can be supported inside the femoral head, close to the articulating surface. The sensor may be situated as close as possible to the articulating contact surface 22 as possible to obtain a temperature reading that is as close as possible to the actual temperature at that contact surface. In the present embodiment the temperature is a miniature temperature sensor (such as ADT7516, Analog Devices, Inc., MA) or thermocouple capable of generating an electrical signal as a function of the ambient temperature. In a specific embodiment, the sensor can be a TD5A miniature temperature sensor sold by MicroSwitch Corp. This sensor is about ⅛ inch in height and width, and less than 1/10 inch in thickness. Other temperature sensors can be used, such as the TC40 thermocouple or the RTD Probe of Minco Products, Inc. The temperature sensor must be small enough to fit within the envelope of a joint component and be capable of providing fast response in a temperature range of 20–200° C.

In accordance with the preferred embodiment, the sensor 30 communicates via internal wiring 33 with a transmission element 35. The transmission element 35 is operable to receive the condition signals from the temperature sensor 30 and transmit an output signal indicative of the condition signal. A power source 40 is electrically connected to the transmission element 35 and the sensor 30 to provide electrical power to both devices via wiring 37 (FIG. 2).

The power source 40 can be an active element, such as a battery, provided that it is suitably small to be supported within an implant component and sufficiently sealed against leakage of toxic materials. A lithium iodine cell available from Wilson Greatbatch Technologies can be used. The power source 40 can include a switch to conserve battery life. The switch can be inductively activated, such as by an electromagnetic wand passed outside the body adjacent the instrumented joint. The switch can be activated when the patient anticipates undertaking activity that will exercise the joint.

Alternatively, the power source 40 can constitute a passive power supply, such as the type of power supply used in RFID tags. This passive power source can be in the form of an inductive ferrite coil, such as the small wound coil available commercially from MicroHelix, Inc. of Portland, Oreg. An external electromagnetic device powers this passive power source.

Figure 2:
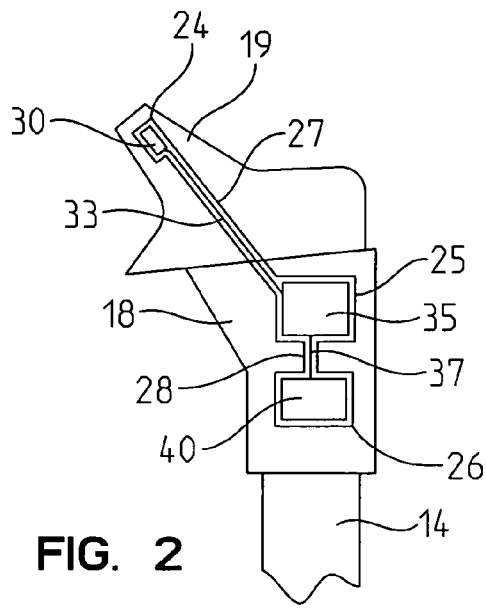
FIG. 2 is a side view of an endoprosthesis according to one embodiment of the present invention.

Referring to FIG. 2, the layout of one embodiment of the invention is illustrated. In particular, the femoral component 14 can be formed with a number of cavities for receiving the elements of the temperature sensing system. Specifically, a cavity 24 can be defined in the neck 19 to receive the sensor 30. The dimensions of the cavity 24 preferably provide a close fit around the sensor. Moreover, the depth of the cavity 24 depends upon the nature of the sensor. In other words, if the sensor requires direct contact with the adjacent tissue, the depth of the channel 24 can be established to allow the sensor to be accessible on the outer surface of the implant. On the other hand, where the sensor is a temperature sensor, as discussed above, the sensor can be embedded within the cavity 24 below the surface of the implant. Most preferably, the temperature sensor is as close to the surface as possible, since its temperature response depends upon heat transmission through the implant into the cavity.

Similar cavities 25 and 26 are defined in the proximal body 18 to house the transmission element 35 and the power source 40, respectively. Wiring channels 27 and 28 pass between the cavities to receive wires 33 and 37, respectively, connected between the elements. The cavities are closed and the elements embedded within a suitable biocompatible material. In a preferred embodiment, bone cement is used to fill the cavities when the sensor 30, transmission element 35 and power supply 40 are housed therein.

The transmission element 35 can take on a variety of forms, all with the purpose of transmitting a signal indicative of the ambient condition within the joint. In a preferred embodiment, the transmission element is a modulator/transmitter that serves to convert the voltage signal received from the temperature sensor into a transmission signal, such as a radio-frequency wave (rf signal), transmitted to a receiver positioned outside the patient's body. Preferably, the transmission element 35 is arranged on a small printed circuit board, which can be of the type commercially available from Advanced Circuits of Aurora, Colo. The particular layout and design of the circuit board will depend upon factors such as the type of electronic components used for the signal source and for modulating the sensor signal.

Suitable internal modulator/transmitters are commercially available from Texas Instruments in the form of electronic chips. While the specific characteristics of the internal modulator/transmitter may vary, the components must be appropriate for implantation within a patient, must transmit at a known frequency and should not consume excessive power. In addition, the transmitter component must be capable of transmitting an rf signal through the patient's body, as well as through the endoprosthesis and/or the potting surrounding the transmission element 35 within the cavity 25. In certain embodiments, the necessary transmission range is not very great, since the receiver will be carried on the patient's body (see below). However, it is contemplated that transmission element may be capable of longer range transmissions, such as to a remote receiver connected to a PC for use in analyzing the ambient conditions within the joint. Various antenna configurations for the transmission element 35 are contemplated by the invention. For instance, the antenna can be situated at the distal end of the implant, where a material that does not impede or restrict the transmissions can replace the metal of the implant. In another configuration, a substantial portion of the implant itself can act as an antenna.

Figure 3:
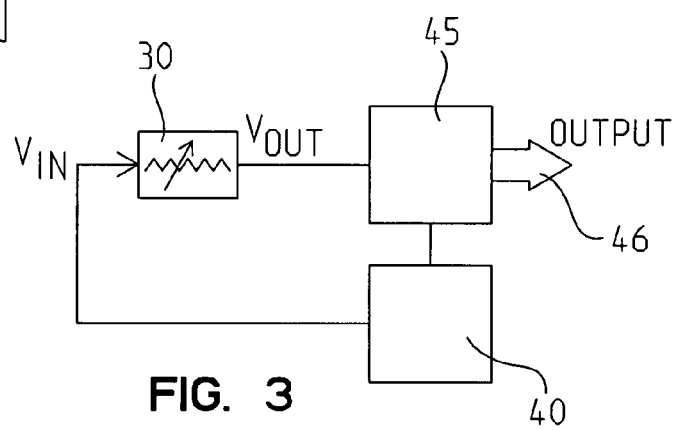
FIG. 3 is a block diagram of the components of the condition sensor system according to an embodiment of the invention for use with the endoprosthesis shown in FIG. 2.
Figure 4A:
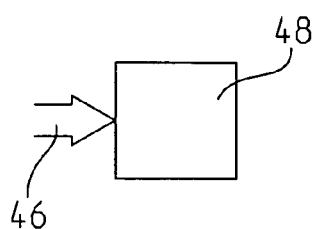
FIGS. 4a and 4b are block diagrams of components for use with the components shown in the block diagram of FIG. 3.
Figure 4B:
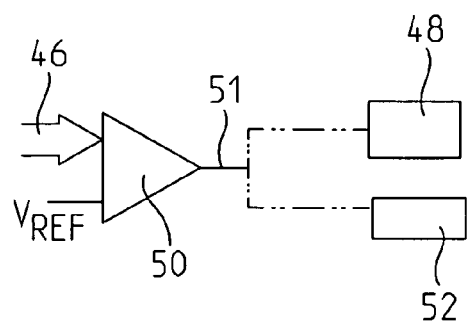

Block circuit diagrams of certain embodiments of the invention are shown in FIGS. 3, 4a and 4b. As depicted in FIG. 3, the temperature sensor 30 can operate as a variable resistor receiving an input voltage from the power source 40. The sensor 30 can be directly electrically connected to the power source or can be connected through the transmission element 25. The sensor 30 produces an output voltage $V_{OUT}$ that is fed to a conditioning circuit 45. The conditioning circuit 45 can constitute the modulator discussed above that converts the voltage $V_{OUT}$ to an rf signal. In this case, the output 46 is an rf signal that is transmitted by an antenna 48, depicted in FIG. 4a. The antenna 48 transmits a signal outside the joint to an external receiver. The transmitted signal or transmission in this embodiment is continuous so that the joint temperature can be continuously monitored.

In an alternative embodiment, a transmission is only if the sensed temperature exceeds a predetermined threshold. In this instance, the conditioning circuit 45 can provides its output 46 to a comparator circuit 50, as shown in FIG. 4b. This comparator circuit 50 can receive a reference voltage $V_{REF}$ from the power source. In this case, the output signal 46 is a voltage, which can be the voltage $V_{OUT}$. The reference voltage $V_{REF}$ can be calibrated to correspond to a threshold temperature as sensed by the temperature sensor. The reference voltage may not necessarily correspond to the actual temperature within the joint, since the temperature sensed by the sensor embedded within the implant body will depend upon the thermal conductivity of the potting material and/or implant material. Nevertheless, an anticipated sensor temperature can be calibrated to an ambient temperature within the joint, and this anticipated temperature translated to a reference voltage $V_{REF}$ that would be generated by the sensor if it was exposed to the threshold temperature.

The output 51 of this comparator circuit can be fed to a transmitter 48. In this case, the comparator circuit 50 would include the modulator feature described above. As an adjunct or another alternative, the output 51 can be a voltage that is fed to an alarm 52 that is resident with the patient, but not necessarily directly associated with the endoprosthesis.

Figure 5:
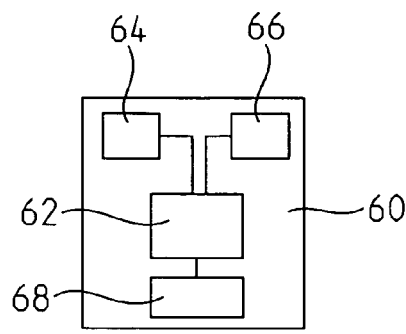
FIG. 5 is a block diagram of an external device according to one aspect of the present invention.

In the most preferred system, the conditioning circuitry 45 is directly coupled to the antenna 48 to continuously transmit a signal indicative of the temperature within the joint. This signal can be received by an external device, such as the devices 60 and 70 shown in FIGS. 5 and 6, respectively. The device 60 in FIG. 5 includes an antenna 62 for receiving the rf signal from the transmission element 35. A power supply 68 supplies power to the antenna, as well as to the other electrical components of the device 60. In addition, the power supply 68 can be configured to provide power to a passive power source 40 mounted within the implant. Thus, the power supply 68 can include a power transmission coil that creates an electromagnetic field intercepted by the passive power source 40. The power supply 68 and the passive power source 40 can utilize RFID tag technology. In some RFID tag systems, the power transmission and signal transmission functions are combined through load modulation. In some passive power systems, the power transmission occurs through dipole antenna transmissions from the external device, while the sensor signal is transmitted through backscatter modulation. The conditioning circuit 45 of the implanted portion of the inventive system can be modified to accomplish either of these forms of power and data transmission.

Returning to FIG. 5, the external device 60 can include an alarm 64 and/or a memory 66. The alarm 64 can provide a sensible signal, such as an audible or touch sensible signal. The alarm 64 can include a piezo-electric component that produces vibration that can be heard and/or felt. A suitable alarm can be the type used in cellular phones, provided that a sufficient power supply is available. The memory 66 can be configured to store a sampling of the received transmission to provide a history of the ambient conditions within the joint. This memory 66 can then be extracted by linking the external device 60 to a PC, for instance. This information can be used by medical personnel to track the response of the endoprosthesis and instrumented joint to exertion by the patient. In addition, analysis of this ambient condition history can diagnose potential problems with the implant or with the patient's activity regimen.

Figure 6:
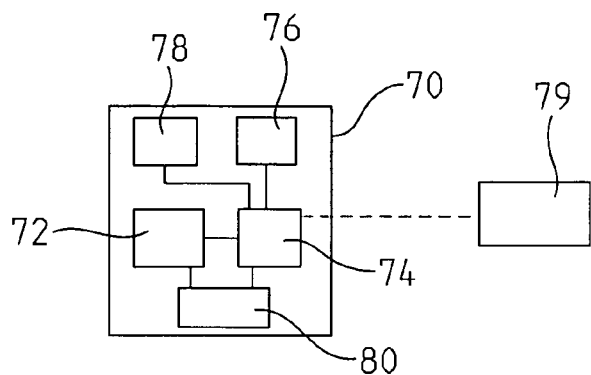
FIG. 6 is a block diagram of an alternative external device according to the invention.

In an alternative embodiment, an external device 70 includes an antenna 72 and analysis circuitry 74, as shown in FIG. 6. This analysis circuitry can evaluate the incoming ambient condition signal received by the antenna 72 and determine a course of action based on that signal. For instance, the analysis circuitry can include a comparator circuit, such as the circuit 50 shown in FIG. 4b, in which the received signal is compared to a threshold value. If the incoming signal exceeds the threshold value, the analysis circuit can send data to an on-board memory 78 and/or activate an alarm 76. The memory and alarm can be configured as described above. A power supply 80 provides power to all of the electronic components of the device 70, and can also serve as a power coil for a passive power source on the endoprosthesis. The analysis circuitry 74 may also provide a link to a visual display device 79. The device 79 can be part of the external device 70 or can be separate from the device and only operable when linked to the analysis circuit 74. In a preferred embodiment, the display device is an LED or LCD array that displays a visual symbol. In the case of a temperature sensor system, the array can display the ambient temperature within the joint. The display device 79 can also display alphanumeric messages indicative of the current condition within the joint, such as "NORMAL" or "WARNING".

The external devices 60 and 70 can be housed within a case and sized to be worn by the patient. For instance, the case housing either device can be strapped around the patient's thigh so that it will be maintained in close proximity to the temperature sensor 30 and transmission element 35. Alternatively, the external devices 60, 70 can be supported on a belt spanning the patient's waist. If the broadcast range of the transmission element is adequate, the external device can be carried anywhere on the person, much like a pager or cell phone.

Figure 7:
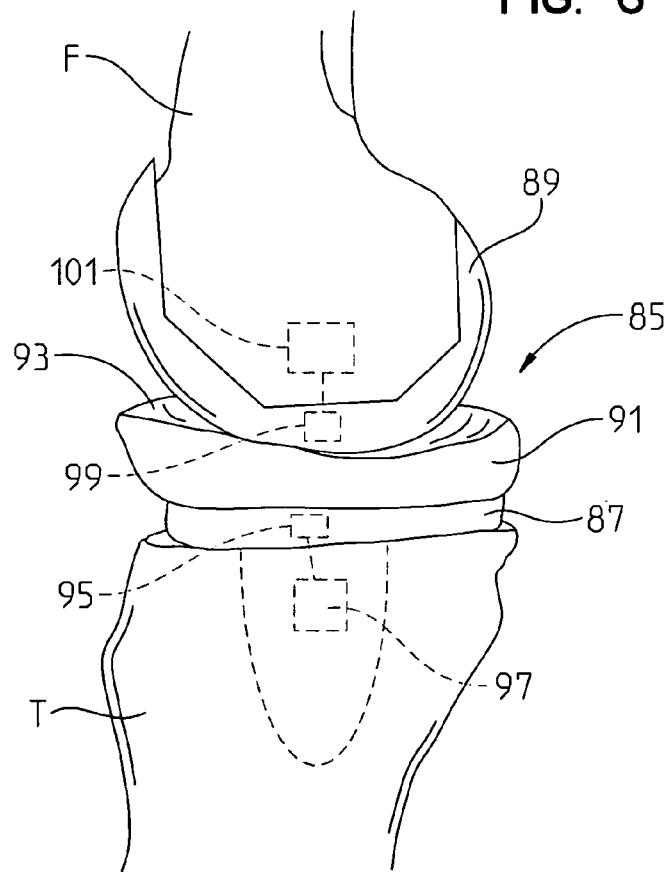
FIG. 7 is a front view of a knee endoprosthesis implementing the ambient condition sensing system of the present invention.

It is contemplated that the present invention can be used in any mammalian joint, including human and animal joints. For instance, the system can be used with a knee endoprosthesis 85, as shown in FIG. 7. By way of background, a typical knee endoprosthesis includes a proximal tibial component 87 that is affixed to the tibia T, distal femoral component 89 that is mounted to the femur F, and an intermediate tibial bearing 91. The tibial bearing 91 and the distal femoral component 89 form the articulating interface 93 as the tibia T moves relative to the femur F. It is at this location that friction between the two components can increase the ambient temperature within the knee joint.

The proximal tibial component 87 includes a tibial temperature sensor 95 that is embedded within the component, preferably as close as possible to the articulating surface 93. The sensor is connected to a transmission element 97 that is embedded within the tibial component as well. The sensor 95 and transmission element 97 can be stacked within a bore defined in the proximal tibial component 87.

Alternatively, or additionally, a temperature sensor 99 can be disposed in the distal femoral component 89. Its associated transmission element 101 can be mounted within a bore defined in the distal end of the femur F, as shown in FIG. 7. The transmission elements 97 and 101 can be configured similar to the transmission element 35 discussed above. A power source, such as the power source 40, can also be provided with both transmission elements. The variation incorporating the sensor 99 illustrates that the ambient condition sensing system of the present invention can be mounted within the patient's natural bone.

The embodiments of the invention described above utilize a temperature sensor to ascertain the ambient temperature within the instrumented joint. Although a single sensor is described above, the implant or prosthetic joint can include several temperature sensors placed at strategic locations. The sensors can generate sensor signals with a particular signature to identify the location of the sensor.

The invention also contemplates a variety of condition sensors for evaluating other ambient conditions of the joint. For example, the sensor 30 can be a pH sensor to evaluate the acidic or alkaline characteristic of the joint environment. Deviation from an expected pH value may indicate a medical condition that requires attention, such as the presence of infection within the joint. A pH sensor must necessarily be in contact with the tissue surrounding the implant. In this case, the sensor can be flush mounted on an exposed surface of the implant. In the context of the hip implant, the sensor 30 can be moved from the neck 19 to the upper end of the proximal body 18 where it will contact the soft tissues and synovial fluid surrounding the implant. Alternatively, the sensor can be placed apart from the implant in contact with pertinent body tissues. For the knee implant, the sensor can be positioned on an exposed edge of the proximal tibial component 87.

The power requirements for the pH sensor may be different from a temperature sensor. Many pH sensors rely upon a chemical reaction to generate a current. One such pH sensor that is suited for biomedical applications is an iridium oxide based potentiometric electrode sold by SensIrOx Inc. Other similar sensors can be utilized that sense the presence of certain chemicals.

In one application of the present invention, the ambient condition sensor is constantly operating throughout the life of the endoprosthesis. As explained above, an internal or external alarm can be provided to notify the patient of a potentially hazardous temperature level within the joint. Alternatively, an external receiver or reader can be provided to receive signals indicative of temperature or other ambient conditions (such as pH) within the joint.

As a further alternative, the sensor system can be used only for diagnostic purposes. In other word, the ambient condition sensor system is activated only intermittently, and more specifically, it is activated by a physician during a visit to evaluate the success of a newly implanted endoprosthesis. In this case, the power source 40 for the implanted system can be a passive system that is activated by the external device, as described above. The patient can undergo a treadmill evaluation, during which the physician monitors the joint temperature. Where the sensor is a pH sensor, the surgeon can simply activate the implant sensor and assess the transmitted pH data during the treadmill evaluation. In other protocols, a directly powered system can generate and store the condition data for later downloading by the surgeon.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

For instance, in the embodiments described above, a single type of sensor is used to generate ambient condition data. Alternatively, several different sensors can be incorporated into the endoprosthesis. Each of the sensors can be provided with a unique signature so that the data transmitted from the system can be easily interpreted. For example, an endoprosthesis can be provided with a temperature sensor and a pH sensor.

Other types of sensors are also contemplated by the invention, where the sensors are capable of evaluating certain ambient conditions within a joint or in surrounding tissue of body spaces. For instance, the sensor can respond to the presence of a particular gene, protein, chemical, bacteria or similar biological substance. A sensor can also be provided that senses the presence of non-biological chemicals or materials. The nature of the ambient condition will determine the type of sensor and the scope of the information obtained about the endoprosthesis and its surroundings.

What is claimed is:

1. A system for sensing a condition within a mammalian joint comprising:
    an endoprosthesis including a body configured to replace a portion of the joint, the body including a wire channel;
    a sensor supported by said body, said sensor adapted to sense an ambient condition of the mammalian joint and to generate a condition signal indicative of the sensed condition;
    a transmitter connected to said sensor through said wire channel to receive said condition signal and operable to transmit a transmission signal outside the joint indicative of said condition signal;
    a receiver disposed outside the joint for receiving said transmission signal; and
    translation circuitry for translating said transmission signal to a human sensible signal.

2. The system of claim 1, wherein said sensor is a temperature sensor and the ambient condition is temperature.

3. The system of claim 1, wherein said sensor is a pH sensor and the ambient condition is pH.

4. The system of claim 1, wherein said sensor is configured to determine the presence of a biological material.

5. The system of claim 1, wherein said sensor is a configured to sense the presence of a pre-determined liquid.

6. The system of claim 1, wherein said body is a component of a joint prosthesis selected from the group of a hip prosthesis, a knee prosthesis, a shoulder prosthesis and an elbow prosthesis.

7. The system of claim 1, wherein said trqansmitter includes an alarm.

8. The system of claim 1, wherein said transmitter is supported by said body.

9. The system of claim 8, wherein said transmitter includes an antenna and a power source providing power to said antenna.

10. The system of claim 1, further comprising a power source supported by said body and connected to provide power to said sensor and said transmitter.

11. The joint endoprosthesis system of claim 10, wherein said power source is a passive power source.

12. The system for determining a condition within a mammalian joint of claim 1 wherein said translation circuitry includes an alarm.

13. The system for determining a condition within a mammalian joint of claim 12, wherein said alarm is configured to produce an audible signal.

14. The system for determining a condition within a mammalian joint of claim 12, wherein said alarm is configured to produce a vibration.

15. The system for sensing a condition within a mammalian joint of claim 1, wherein said translation circuitry includes a display configured to produce a visually sensible signal.

16. A method for determining a condition within a mammalian joint comprising the steps of:
 introducing a sensor within the joint, the sensor adapted to sense a temperature and to generate a sensor signal indicative of the temperature;
 coupling the sensor with a transmission element operable to transmit an information signal outside the joint in response to the sensor signal;
 sensing the ambient condition within the joint;
 transmitting the information signal;
 analyzing the information signal to determine when a temperature within the joint exceeds a predetermined setpoint; and
 generating a human sensible warning signal in response to the determination that the temperature within the joint exceeds a predetermined setpoint.

17. The method for determining a condition within a mammalian joint of claim 16, wherein introducing a sensor within the joint comprises:
 placing the sensor within a ball portion of a prosthetic device used in a ball and socket joint.

18. The method for determining a condition within a mammalian joint of claim 17, further comprising:
 placing a second sensor within a socket portion of a prosthetic device used in the ball and socket joint.

19. The method of claim 16, wherein coupling the sensor with a transmission element comprises:
 connecting the sensor to the transmitter through a wire channel in a prosthetic device.

* * * * *